United States Patent [19]

Sluetz et al.

[11] E Patent Number: Re. 31,990

[45] Reissued Date of Patent: Sep. 24, 1985

[54] MULTIPLE FUNCTION LEAD ASSEMBLY AND METHOD FOR INSERTING ASSEMBLY INTO AN IMPLANTABLE TISSUE STIMULATOR

[75] Inventors: James E. Sluetz, Lake Jackson; Richard V. Calfee, Houston, both of Tex.

[73] Assignee: Intermedics, Inc., Angleton, Tex.

[21] Appl. No.: 409,162

[22] Filed: Aug. 18, 1982

Related U.S. Patent Documents

Reissue of:

[64] Patent No.: 4,236,525
Issued: Dec. 2, 1980
Appl. No.: 963,128
Filed: Nov. 22, 1978

[51] Int. Cl.[4] ..... A61N 1/36

[52] U.S. Cl. ..... 128/419 P; 128/784

[58] Field of Search ..... 128/419 P, 784–786; 339/16 R, 18 R, 18 P, 60 R, 60 C, 60 M, 61 R, 61 C, 63 R, 63 M, 65, 94 R, 116 R, 116 C

[56] References Cited

U.S. PATENT DOCUMENTS

| | | | |
|---|---|---|---|
| 3,641,479 | 2/1972 | O'Brien et al. | 339/94 R |
| 3,649,367 | 3/1972 | Purdy | 128/419 P |
| 3,649,948 | 3/1972 | Porter | 339/16 R |
| 3,768,487 | 10/1973 | Rose | 128/419 P |
| 3,866,615 | 2/1975 | Hewson | 128/784 |
| 4,072,154 | 2/1978 | Anderson et al. | 128/419 P |
| 4,112,953 | 9/1978 | Shanker et al. | 128/419 P |

FOREIGN PATENT DOCUMENTS

| | | |
|---|---|---|
| 1589585 | 4/1970 | Fed. Rep. of Germany . |
| 1517201 | 3/1968 | France . |

OTHER PUBLICATIONS

U.S.C.I. Catheter Catalogue No. 5070105, Sec. 5, Jun., 1974, pp. 1–12.

The Design of an Implantable Cardiac Pacemaker by R. D. McDonald, Medical and Biological Engineering, vol. 4, pp. 137–152, Pergamon Press, 1966.

*Primary Examiner*—William E. Kamm

*Attorney, Agent, or Firm*—Willian Brinks Olds Hofer Gilson & Lione Ltd.

[57] ABSTRACT

Apparatus and methods are provided for manually altering the function of the distal electrodes of a body implantable tissue stimulator assembly. In one exemplary embodiment, the polarity of distal electrodes may be reversed by axially repositioning the proximal connectors within the female connector assembly of a tissue stimulator.

21 Claims, 9 Drawing Figures

MULTIPLE FUNCTION LEAD ASSEMBLY AND METHOD FOR INSERTING ASSEMBLY INTO AN IMPLANTABLE TISSUE STIMULATOR

Matter enclosed in heavy brackets [ ] appears in the original patent but forms no part of this reissue specification; matter printed in italics indicates the additions made by reissue.

FIELD OF THE INVENTION

This invention relates generally to tissue stimulation devices, amd more particularly relates to body implantable devices for stimulation and sensing of body organ fuctions. In a specific embodiment of the present invention, the function of distal electrodes connected to the output of a tissue stimulator may be altered by moving the proximal connectors axially within the female connector assembly of the stimulator.

BACKGROUND OF THE INVENTION

It is well known that certain body organs, notably the heart, bladder, phrenic nerve, and carotid sinus are susceptible to artificial stimulation and sensing, employed when their natural functioning becomes impaired in some manner. Artificial stimulation is normally accomplished by the implantation into the body of the patient of an electrical pulse generator which is connected to the tissue of the failing organ through an electrically conductive lead assembly. The distal end of this lead assembly is placed into contact with the tissue of the organ, while the proximal end is placed into contact with the output terminals of the pulse generator. A well known example, discussed herein by way of example and not of limitation, of this medical technique concerns stimulation of the human heart.

Heart stimulators and lead assemblies are well known, and have been of two general types: unipolar or bipolar. In a unipolar device, the stimulator has a single output terminal, and the metallic case of the device serves as the complementary electrode. Thus, the stimulating impulse can be supplied to the heart or other tissue via a single conductor lead, and the circuit is completed through body tissue and fluids. In a bipolar device, the stimulator has two output terminals, and the case plays no part in the circuit. This type stimulator utilizes a two conductor lead, each conductor terminating in a distal electrode. Such a two conductor lead may also find application with unipolar devices having a sensing input. In this situation, one conductor would handle impulse transmission to the heart or other tissue, while the other conductor relays information about the selected tissue back to the stimulator.

After implanting such a device and its lead assembly into the body of a patient, the physician will check the minimum effective impulse level, or threshold, of the distal electrodes to verify electrical contact with the heart, or other tissue, to assure proper stimulator and sensing thresholds. At this time, in the case of a two conductor lead assembly, the physician may discover that a better stimulating threshold exists at the complementary electrode of a bipolar stimulator, or at the sensing electrode of a unipolar stimulator. If this occurred, the physician would want to change the function of these electrodes so that stimulating pulses could be accomplished through the electrode having the most advantageous threshold condition.

Another situation that may develop occurs when, over a period of time, fibrotic (and scar tissue caused by the contact between the distal electrodes and the heart) growth alters the threshold characteristics at the primary stimulating electrode. Again, to improve this situation, the physician might want to stimulate through the secondary electrode.

To correct either of these situations, the physician could reposition the primary electrode in the hope of locating a position with a more favorable threshold. At the time of implantation, this relocation would be possible, but extremely difficult. However, to attempt a relocation after fibrotic growth has overtaken the electrodes could very possibly result in traumatic injury to heart tissue and venous connecting paths.

Most prior art lead and stimulator assemblies have been designed to function in only one configuration.

Where provision has been made for altering an electrode function, the resulting female connector assembly design has remained bulky at a time when implanted assemblies and leads were being reduced in size to facilitate implantation. These same conditions and problems exist with body implantable tissue stimulators utilized with the other body organs susceptible to artificial stimulation.

To overcome the disadvantages of prior art tissue stimulators and lead assemblies, apparatus and methods are provided to allow a physician to conveniently alter the function of a lead assembly, either at the time of implantation, or later, if the heart's reaction to the presence of the distal electrodes indicates that a change would be advantageous.

Accordingly, it is a feature of the invention to provide a reduced volume female connector and electrode assembly which permits alteration of the function of the distal electrodes of the lead assembly.

It is a further feature of the invention to accomplish this alteration of function by only axial relocation of the proximal connector assembly.

One other feature is a reversible function electrode assembly having coaxial proximal connectors spaced axially apart.

It is an object of the present invention to provide for altering the stimulus from an electrode without physical relocation of an implanted distal electrode.

Another object is to provide a variable function female connector assembly with a space envelope of a single function female connector assembly.

*Another object of the invention is to provide a method for reversing the function of an electrode assembly of a tissue stimulator.*

*A further object of the invention is to provide a method and apparatus for conductively connecting a multiple function lead assembly with a female connector assembly of a tissue stimulation device to permit alteration of the function of distal tissue stimulation electrodes of the lead assembly.*

SUMMARY OF THE INVENTION

A lead assembly for a body implantable tissue stimulator is provided with a plurality of distal electrodes which have alterable electrical characteristics. Proximal connectors are interconnected with the distal electrodes and are in electrical contact with the tissue stimulator. The proximal connectors are coaxial and axially spaced for mating with corresponding stimulator output electrodes. The axial spacing provides a minimum profile assembly and permits altering distal electrode characteristics by only axially repositioning the proximal connectors.

BRIEF DESCRIPTION OF THE DRAWINGS

So that the manner in which the above recited features, advantages, and objects of the present invention, as well as others, which will become apparent, are attained and understood in detail, a more particular description of the invention may be had by reference to specific embodiments thereof which are illustrated in the appended drawings, which drawings form a part of this specification. It is to be noted, however, that the appended drawings illustrate only typical embodiments of the invention, and therefore are not to be considered limiting of its scope, for the invention may admit to further equally effective embodiments.

In the Drawings

DETAILED DESCRIPTION OF THE DRAWINGS

Figure 1:
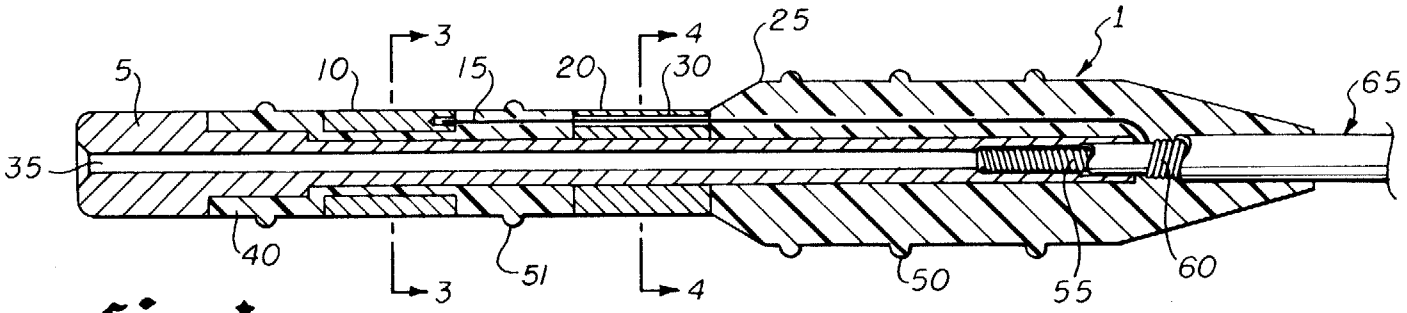
FIG. 1 is a cross-sectional side view of a three electrode proximal connector of a bipolar lead assembly.

Referring first to FIG. 1, there may be seen a proximal connector assembly 1 which interconnects with an implanted tissue stimulator generator assembly, as hereinbelow described. A connector seal plug 25 sealingly mates with a generator female connector assembly (not shown) and is provided with sealing ribs 50 to assist in inhibiting the leakage of body fluids into the interstitial cavity of the female connector assembly.

Insulated conductor assembly 65 interconnects proximal connector assembly 1 with an exposed electrode assembly (not shown) which is adjacent the tissue portion which is to be stimulated. In the embodiments hereinbelow discussed, reference will be made to a bipolar electrode unit, wherein there are two exposed electrodes adjacent the tissue. It will be readily apparent that any number of electrodes may be provided and the proximal connector electrodes cascaded in the manner hereinbelow described. Any such cascaded arrangement is contemplated by, and is within the scope of the present invention.

Figure 2:
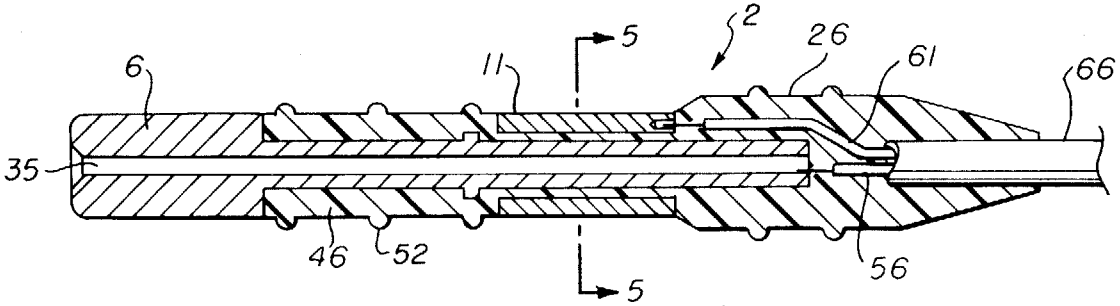
FIG. 2 is a cross-sectional side view of a two electrode proximal connector of a bipolar lead assembly.

As shown in FIG. 1, conductor assembly 65 may conveniently consist of a first conductor 55 and a second conductor 60. Conductors 55 and 60 are preferably formed in a spiral configuration in order to provide a flexible conductor assembly 65 with improved fatigue characteristics to endure the continuous flexing experienced in an implanted environment. FIG. 1 depicts a coaxial arrangement for conductors 55 and 60 wherein conductor 55 is interior of, and insulated from, conductor 60. A side-by-side arrangement of conductors 55 and 60 with an intervening insulator might also be used, and such an arrangement is depicted in FIG. 2.

Conductors 55 and 60, each of which are connected with a separate exposed electrode adjacent the tissue stimulated, are interconnected with electrodes in proximal connector assembly 1. As depicted in FIG. 1, three electrodes are provided in proximal connector 1 and extending from seal plug 25. A first electrode 5 and a second electrode 20 are electrically connected with first conductor 55. First electrode 5 may be conveniently formed to obtain an exposed portion adjacent the outer end of the electrode assembly and having an interior portion extending therethrough to make electrical contact with first conductor 55.

In a preferred embodiment, a second electrode 10 is provided, which may conveniently be formed as a cylinder concentric with the internal portion of electrode 5. Second electrode 10 is interconnected with second conductor 60 by connecting wire 15 which extends from second conductor 60 through an aperture 30 extending along the interior portion of first electrode 5 and through third electrode 20.

Various insulator assemblies are required to maintain the electrical isolation of the various tip electrodes 5, 10, and 20. A first insulator portion 45 may be formed between second conductor 10 and third conductor 20 and may also incorporate a sealing rib 51, if desired, to firmly hold the electrode tip assembly within the generator female connector assembly (not shown). A second insulator portion 40 is provided to isolate first electrode 5 from second electrode 10. As depicted in FIG. 1, second insulator portion 40 is formed to provide axial insulation between the exposed portion of first electrode 5 and second electrode 10 and to also provide radial insulation between second electrode 10 and the interior portion of first electrode 5 extending therethrough. A sealing rib 51 may be formed on the axially insulating portion of second insulator portion 40, also for the purpose of firmly engaging the generator female connector assembly (not shown).

In many instances, implanted lead assemblies for tissue stimulation require that the flexible lead assembly be moved through and along a convoluted path. In order to accomplish this, the stiffness of the lead assembly is increased during insertion by a stylet (not shown) which is insertable through aperture 35 and interiorly of second conductor 55. The stylet provides longitudinal rigidity while permitting sufficient flexure for the lead to traverse the required path.

In FIG. 2, there may be seen a two electrode version of the proximal connector assembly 2. A connector seal plug 26 is provided as hereinabove discussed for seal plug 65 in FIG. 1. Insulated conductor assembly 66 is mated with seal plug 26.

A parallel arrangement for first conductor 56 and second conductor 61 is shown. Each of the conductors 56 and 61 is spirally wound for the reasons hereinabove set forth. It is apparent that the coaxial lead assembly 65 depicted in FIG. 1 could be substituted for conductor assembly 66. A coaxial electrode configuration as depicted in FIG. 1 is generally preferred because the overall diameter of conductor assembly 65 is somewhat less than conductor assembly 66. However, a final preferred arrangement will depend on the number of electrodes which are being interconnected.

Referring again to FIG. 2, a first electrode 6 and second electrode 11 are provided in proximal connector assembly 2. First electrode 6 includes an exposed portion and an interior portion extending to connect with first conductor 56. A second conductor 11 is shown coaxial with the interior portion of first conductors 6 and extending through seal plug 26 to make electrical contact with second conductor 61.

First electrode 6 and second electrode 11 are electrically isolated by insulator 46. Insulator 46 has a first portion for axially insulating between first conductor 6 and second conductor 11 which may have a sealing rib 52 and a second portion for radially insulating the interior portion of first electrode 6 on the concentric second electrode 11.

Thus, FIG. 1 depicts a first electrode arrangement having three axially spaced electrodes. First electrode 5 and third electrode 20 are electrically interconnected and both connected with a first conductor 55. A second electrode 15 is electrically isolated from first electrode 5 and third electrode 20 and is electrically connected with conductor 60. In FIG. 2, there is depicted a two electrode assembly, with first electrode 6 electrically connected with conductor 56. Second electrode 11 is axially and radially isolated from first electrode 6 and is connected with second conductor 61.

Figure 3:
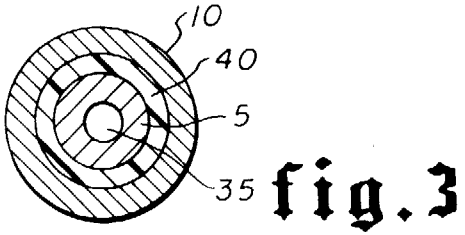
FIG. 3 is a cross-section through the center electrode shown in FIG. 1.

Referring now to FIG. 3, there is shown a cross-section taken along 3—3 shown in FIG. 1. Second electrode 10 is radially insulated from the inner portion of first electrode 5 by second insulator portion 40. Annular space 35 provides the opening for inserting a stylet therethrough.

Figure 4:
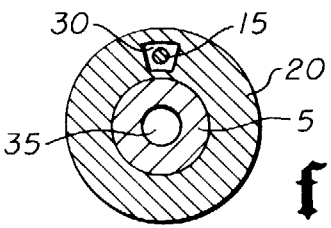
FIG. 4 is a cross-section through the inside electrode shown in FIG. 1.

Referring now to FIG. 4, there is depicted a cross-section through 4—4 as shown in FIG. 1. Third electrode 20 is conveniently formed as a cylinder to fit about the interior portion of first electrode 5. Thus third electrode 20 electrically connects with first electrode 5. Third electrode 20 further defines annular space 30 through which connector wire 15 is inserted to connect the second electrode with the corresponding conductor.

Figure 5:
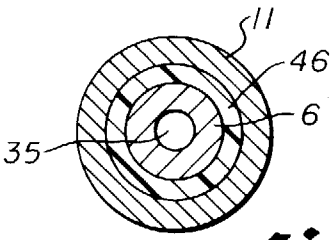
FIG. 5 is a cross-section through the inside electrode shown in FIG. 2.

Referring now to FIG. 5, there is depicted a cross-section viewed through 5—5 as shown in FIG. 2. Second electrode 11 is isolated from the interior portion of first electrode 6 by insulating material 46. As shown in FIG. 2, second electrode 11 may conveniently extend coaxially with the inner portion of first electrode 6 throughout generally the length of first electrode 6 to make electrical contact with second conductor 61.

Figure 6:
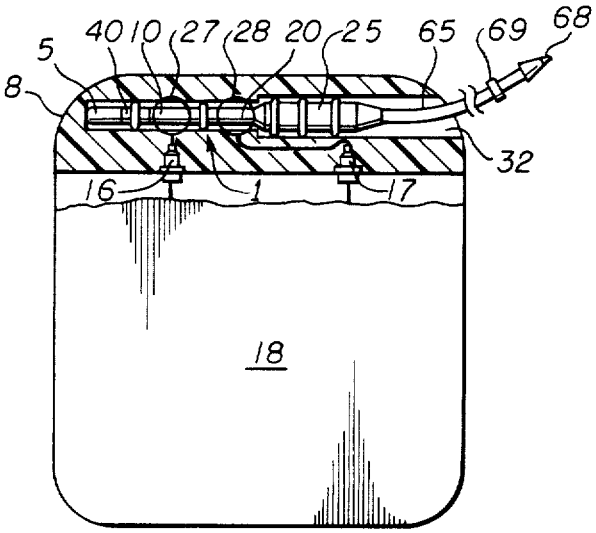
FIG. 6 is a side view of a tissue stimulator with FIG. 1 connector in a first position.

Referring now to FIG. 6, there may be seen the proximal connector assembly 1, hereinabove discussed in FIG. 1, engaged within stimulator female connector assembly 8. Distal electrodes 68 and 69 are shown in assembly with insulated conductor assembly 65. In one embodiment, tip electrode 68 is the stimulating electrode and may conveniently be interconnected through the interior spiral conductor if a coaxial conductor arrangement is used, and thereafter interconnected with first electrode 5 and third electrode 28, as hereinabove explained. The second distal electrode 69 may conventionally be a sensing electrode or may serve as a ground or return path for the stimulating electrode 68 output. Electrode 69 may conveniently be connected to the external spirally wound coil, where a coaxial coil is used, and connected with second electrode 27.

In FIG. 6, there is depicted a first inserted arrangement of proximal connector assembly 1. Stimulator female connector assembly 8 generally defines cavity 32 for accepting proximal connector assembly 1. In a conventional assembly, electrical components and the stimulator battery are enclosed within a sealed case 18 with first output electrode 16 and second output electrode 17 sealingly interconnected through case 18. Output electrodes 16 and 17 are electrically connected with releasable connectors 27 and 28, respectively, which may conveniently be set screws for securely engaging the electrode portions of proximal connector 1.

As depicted in FIG. 6, second electrode 10 is adjacent releasable connector 27 and third electrode 20 is adjacent releasable connector 28. Connectors 27 and 28 are secured against electrodes 10 and 20, respectively, to establish the required electrical contact. Removable plug members may be placed over connectors 27 and 28 in order to prevent the leakage of body fluids into cavity 32 adjacent the various electrical components and may generally be formed of bio-compatible materials. Connector seal plug 25 sealingly engages the walls defining cavity 32 to preclude entry of body fluids into the region of cavity 32 containing the various electrode components.

If it is determined at a later date that it would be desirable to alter the functions of distal electrodes 68 and 69, or to reverse the connection for other reasons, such a reversal is easily accomplished as hereinbelow shown in FIG. 7. Releasable connectors 27 and 28 are loosened, and the proximal connector assembly 1 is moved axially to a second position. It may be seen in FIG. 7, that first electrode 5 is now adjacent releasable connector 27 and second electrode 10 is now adjacent releasable connector 28.

Figure 7:
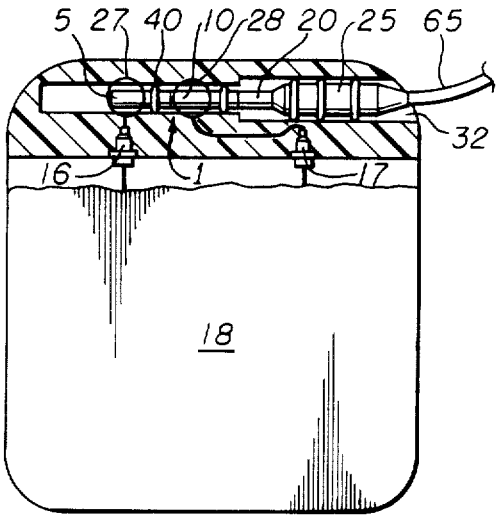
FIG. 7 is a side view of a tissue stimulator with FIG. 1 connector in a second position.

Once proximal connector assembly 1 has been moved to the position shown in FIG. 7, releasable connector 27 is secured against first connector 5, thereby interconnecting electrode 5 with output electrode 16. Releasable connector 28 is secured against second electrode 10, securing electrical contact between second conductor 10 and output electrode 17. Thus, the desired change in the electrode connections has been effected and distal electrodes 68 and 69 are now electrically connected with different output electrodes from the implanted tissue stimulator. It will be appreciated that this reconnection has been achieved without relocating distal electrodes 68 and 69 or even removing the implanted tissue stimulator case 18 and female connector assembly 8.

The electrode interconnection change, hereinabove discussed, can be used to make the stimulating electrode a sensing electrode; make the ground return electrode a stimulating electrode; or to alter the output in any fashion as distinguished by the output from electrodes 16 and 17.

Figure 8:
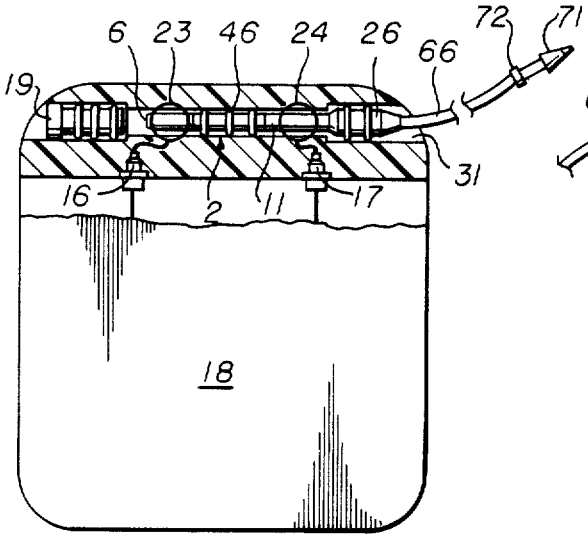
FIG. 8 is a side view of a tissue stimulator with FIG. 2 connector in a first position.

Referring now to FIG. 8, there is shown proximal connector assembly 2 inserted in female connector assembly 9. Distal electrodes 71 and 72 are provided and electrically interconnected through insulated conductor assembly 66 to first electrode 6 and second electrode 11. It will be assumed for discussion purposes that distal electrode 71 is connected with first electrode 6, and distal electrode 72 is connected with second electrode 11. It is readily apparent that the reverse connection could easily be made. Female connector assembly 9 defines cavity 31 which extends longitudinally entirely through female connector assembly 9. A removable seal plug 19 may be used to seal the open end of cavity 31 to prevent the entry of body fluids into the electrode-containing portions of female connector assembly 9. If desired, a seal plug could be conveniently provided adjacent first electrode 6 for sealing entry into cavity 31. Seal plug 26 is provided for sealing the other entry into cavity 31.

Thus, as depicted in FIG. 8, releasable connector 23 is adjacent first electrode 6, and releasable connector 24 is adjacent second electrode 11. As hereinabove discussed, releasable connectors 23 and 24 may conveniently be set screws and may incorporate sealing means of a suitable bio-compatible material for excluding body fluids. Thus, when connectors 23 and 24 are tightened, first electrode 6 is electrically connected to output electrode 16 and the second electrode is electrically connected to output electrode 17, respectively. Output electrodes 16 and 17 sealingly extend from case 18 which encloses the stimulator pulse generator circuitry and battery.

Figure 9:
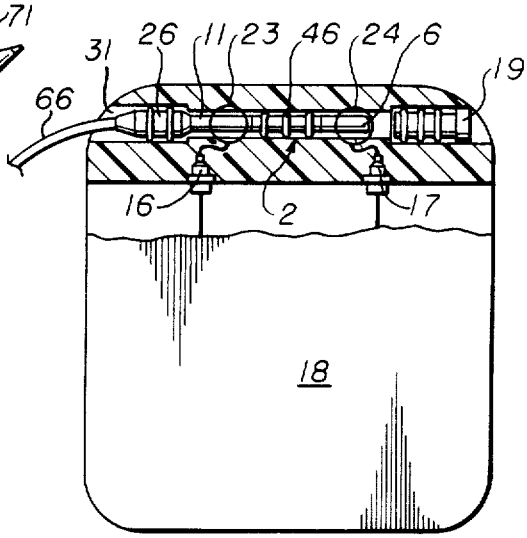
FIG. 9 is a side view of a tissue stimulator with FIG. 2 connector in a second position.

In FIG. 9, there may be seen proximal connector assembly 2 axially repositioned to effect a change in electrode connections. In this instance, the axial repositioning requires that seal plug 19 be removed from within cavity 31 and proximal connector assembly 2 removed from cavity 31. Proximal connector 2 is reinserted in the opposite opening of cavity 31, previously occupied by seal plug 19. Seal plug 19 then seals the opening not occupied by proximal connector assembly 2. For the electrode assembly depicted in FIGS. 8 and 9, a sufficient length of conductor assembly 66 may be conveniently provided in the original implantation whereby proximal connector assembly 2 may be moved to the opposite side of cavity 31. Conductor assembly 66 may be easily repositioned to accommodate this relocation. Alternately, female connector assembly 9 and case 18 may be turned over to reposition the opening into cavity 31 adjacent proximal connector assembly 2.

Thus, as shown in FIG. 9, first electrode 6 is now adjacent releasable connector 24 and second electrode 11 is adjacent releasable connector 23. Connectors 23 and 24 are secured to connect second electrode 11 with output electrode 16 and first electrode 6 with output electrode 17, respectively. The openings into cavity 31 are sealed by plug 19 and connector seal plug 26.

It will be thus apparent that the above embodiments of the present invention are well adapted to provide for variably connecting distal electrodes with tissue stimulator generator output electrodes. As hereinabove shown, only an axial repositioning of the connectors is required to vary the interconnections, wherein the various female connector assemblies are sized to accommodate only a single electrode cavity therethrough.

Numerous variations and modifications may obviously be made in the structure herein described without departing from the present invention. Accordingly, it should be clearly understood that the forms of the invention herein described and shown in the figures of the accompanying drawings are illustrative only and are not intended to limit the scope of the invention.

What is claimed is:

1. Apparatus for connecting a body implantable tissue stimulator and lead assembly, comprising at least two distal electrodes on said lead assembly for electrical stimulation or sensing, at least [two] *three* coaxial proximal connectors on said lead assembly spaced apart and [electrically] *conductively* connected to said distal electrodes for connecting said distal electrodes with said *implantable* tissue [stimulation means] *stimulator, two of said three proximal connectors conductively connected to one of said two distal electrodes and the remaining one of said three proximal connectors conductively connected to the other of said two distal electrodes,* a female connector assembly [on] *of* said body implantable tissue stimulator [adapted to electrically connect] *for conductively connecting at least two of* said proximal connectors to said stimulator, insulator means intermediate adjacent ones of said coaxial proximal connectors [having fluid sealing ribs cooperating with said female connector assembly] for maintaining fluid isolation between said connectors.

[2. The apparatus described in claim 1, wherein said at least two distal electrodes comprises two electrodes, and said at least two proximal connectors comprises two connectors.]

[3. The apparatus described in claim 1, wherein said at least two distal electrodes are two distal electrodes; and said at least two proximal connectors are three proximal connectors;

two of said three proximal connectors being connected to a first of said two distal electrodes, and the remaining one of said three proximal connectors being connected to a second of said two distal electrodes.]

4. The apparatus described in claim [3] *1*, wherein said two proximal connectors bracket said remaining one proximal connector.

5. The apparatus described in claim 1, wherein said tissue [stimulation means] *stimulator* comprises a female connector assembly having connection means for removably securing [said at least two] *at least two of said* proximal connectors in electrical contact with said tissue [stimulation means] *stimulator.*

6. The apparatus described in claim 5, wherein said connection means are located to align with two of said [at least two] proximal connectors when [said at least] *the* two proximal connectors are inserted therein.

7. A body [implantable lead assembly,] *function assistance device, comprising:*

*a body implantable tissue stimulator including a female connector assembly,* [comprising]

*a lead assembly for conductively engaging said female connector assembly,* at least two distal electrodes [on] *of* said lead assembly for electrical stimulation or sensing, at least [two] *three* coaxial proximal connectors [on] *of* said lead assembly axially spaced apart and [electrically] *conductively* connected with said distal electrodes, *two of said three proximal connectors being connected to a first of said two distal electrodes, and the remaining one of said three proximal connectors being connected to a second of said two distal electrodes,* and insulator means intermediate adjacent ones of said at least [two] *three* coaxial proximal connectors and having at least a portion with a diameter greater than the diameter of said adjacent electrodes, *said at least a portion of the insulator means configured and adapted to act as a fluid sealing rib and to cooperate with the female connector assembly of the body implantable tissue stimulator to maintain fluid isolation between said proximal connectors.*

[8. The apparatus described in claim 7, wherein said at least two distal electrodes comprises two electrodes and said at least two proximal connectors each comprises two connectors.]

[9. The apparatus described in claim 7, wherein said at least two distal electrodes are two distal electrodes; and said at least two proximal connectors are three proximal connectors;

two of said three proximal connectors being connected to a first of said two distal electrodes, and the remaining one of said three proximal connectors being connected to a second of said two distal electrodes.]

*10. A body implantable tissue stimulation system comprising:*

*a body implantable lead comprising:*

*first and second distal electrodes;*

*a proximal electrode assembly; and*

*first and second conductors extending between the proximal electrode assembly and the first and second distal electrodes, respectively;*

*a body implantable stimulator comprising:*

*first and second stimulator electrodes; and*

*means for defining a channel in the stimulator adjacent the stimulator electrodes, said channel dimensioned to receive the proximal electrode assembly such that the proximal electrode assembly is movable axially between first and second axial positions without removing the proximal electrode assembly from the channel; and*

*means for interconnecting the first and second stimulator electrodes with the first and second conductors in accordance with the axial position of the proximal electrode assembly in the channel, said interconnecting means operative to interconnect the first stimulator electrode with the first conductor and the second stimulator electrode with the second conductor when the proximal electrode assembly is in the first axial position, and to interconnect the first stimulator electrode with the second conductor and the second stimulator electrode with the first conductor when the proximal electrode assembly is in the second axial position;*

*said lead, stimulator, and connecting means cooperating to allow an interchange of the functions of the distal electrodes without removing the proximal electrode assembly from the channel.*

*11. The invention of claim 10 wherein the interconnecting means comprises:*

*first, second, and third coaxial, axially spaced proximal electrodes mounted on the proximal electrode assembly;*

*means for interconnecting the first and third proximal electrodes with the first conductor;*

*means for interconnecting the second proximal electrode with the second conductor; and*

*means for insulating the second proximal electrode from the first and third proximal electrodes;*

*said second proximal electrode situated intermediate of said first and third proximal electrodes.*

*12. The invention of claim 11 wherein the insulating means comprises:*

*a first sealing rib situated between the first and second proximal electrodes; and*

*a second sealing rib situated between the second and third proximal electrodes;*

*said first and second sealing ribs extending radially outwardly between the first, second, and third proximal electrodes and dimensioned and adapted to seal the channel between adjacent proximal electrodes in order to maintain fluid isolation between adjacent proximal electrodes.*

*13. A body implantable stimulation system comprising:*

*a body implantable lead comprising:*

*first and second distal electrodes;*

*a proximal electrode assembly comprising first, second, and third coaxial, axially spaced proximal electrodes;*

*means for electrically connecting the first and third proximal electrodes with the first distal electrode;*

*means for electrically connecting the second proximal electrode with the second distal electrode; and*

*means for insulating the first and third proximal electrodes from the second proximal electrode;*

*said second proximal electrode situated intermediate of the first and third proximal electrodes;*

*a body implantable stimulator comprising:*

*first and second stimulator connectors; and*

*means for receiving the proximal electrode assembly adjacent the first and second connectors;* said receiving means configured such that the proximal electrode assembly is movable along an axis between a first portion, in which the first connector is electrically connected with the first distal electrode via the first proximal electrode and the second connector is electrically connected with the second distal electrode via the second proximal electrode, and a second axial position, in which the first connector is electrically connected with the second distal electrode and the second connector is electrically connected with the first distal electrode via the third proximal electrode.

*14. The invention of claim 13 wherein the receiving means comprises means for defining a bore and wherein the lead comprises at least two sealing ribs, each disposed between a respective adjacent pair of the proximal electrodes, said sealing ribs each extending radially outwardly from the proximal electrodes and dimensioned to create a seal against the means for defining the bore so as to maintain fluid isolation of the three proximal electrodes from one another when the proximal electrode assembly is positioned within the bore.*

*15. A method for coupling a body implantable lead to a body implantable stimulator comprising the following steps:*

*(a) providing a body implantable lead comprising:*

*first and second distal electrodes;*

*a proximal electrode assembly comprising first and second coaxial, axially spaced proximal electrodes;*

*means for electrically connecting the first proximal electrode with the first distal electrode and the second proximal electrode with the second distal electrode; and*

*means for electrically insulating the first and second proximal electrodes;*

*(b) providing a body implantable stimulator comprising:*

*first and second stimulator connectors; and*

*means for receiving the proximal electrode assembly adjacent the first and second stimulator connectors, said receiving means defining a channel having first and second ends;*

*(c) inserting the proximal electrode assembly into the first end of the channel and positioning the proximal electrode assembly in the channel such that the first stimulator connector is electrically connected to the first distal electrode via the first proximal electrode and the second stimulator connector is electrically connected to the second distal electrode via the second proximal electrode; then*

*(d) removing the proximal electrode assembly from the channel; and then*

(e) inserting the proximal electrode assembly into the second end of the channel and positioning the electrode assembly in the channel such that the first stimulator connector is electrically connected to the second distal electrode via the second proximal electrode and the second stimulator connector is electrically connected to the first distal electrode via the first proximal electrode, thereby reversing the connections of the first and second distal electrodes.

16. The invention of claim 15 wherein the insulating means further comprises:

at least one sealing rib positioned between the first and second proximal electrodes to extend radially outwardly from the proximal electrodes, said sealing rib dimensioned and adapted to contact the channel to create a seal against the channel between the first and second proximal electrodes in order to maintain fluid isolation therebetween.

17. A body implantable tissue stimulation system comprising:

a body implantable lead comprising:

first and second distal electrodes;

a proximal electrode assembly which comprises at least first and second coaxial, axially spaced proximal electrodes, each of which is electrically connected with a respective one of the distal electrodes, a third coaxial axially spaced proximal electrode electrically connected with the first proximal electrode and situated such that the second proximal electrode is interposed between the first and third proximal electrodes; and means for electrically insulating the first proximal electrode from the second proximal electrode and the second proximal electrode from the third proximal electrode;

a body implantable tissue stimulator comprising:

first and second stimulator electrodes; and means for defining a channel in the stimulator adjacent the stimulator electrodes to receive the proximal electrode assembly in order to establish electrical contact between the stimulator electrodes and respective ones of the proximal electrodes; and means for creating a fluid seal in the channel between the tissue stimulator and the proximal electrode assembly in order to maintain fluid isolation between at least two of the proximal electrodes.

18. The invention of claim 17 wherein the means for creating a seal comprises a fluid sealing rib mounted on the insulating means to extend radially outwardly from the proximal electrodes to contact and seal against the channel defining means.

19. The invention of claim 17 wherein the means for creating a seal comprises a first fluid sealing rib mounted on the means for insulating the first proximal electrode from the second proximal electrode to extend outwardly from the proximal electrodes to contact and seal against the channel defining means, and wherein the invention further comprises a second fluid sealing rib mounted on the means for insulating the third proximal electrode from the second proximal electrode to extend outwardly from the proximal electrodes to contact and seal against the channel defining means in order to maintain fluid isolation between the second and third proximal electrodes.

20. A body tissue stimulation apparatus, comprising:

a body implantable tissue stimulator for generating electrical stimulation signals;

a body implantable lead assembly for sealingly and conductively engaging said tissue stimulator and for applying said stimulation signals to a predetermined site of the body;

said lead assembly including, two distal electrodes positioned at said site for applying said stimulation signals;

three spaced coaxially aligned proximal connectors;

means for conductively connecting one of the distal electrodes to two of the proximal connectors; and means for conductively connecting the other of the distal electrodes to the third proximal connector;

said tissue stimulator including two terminals for adjustably conductively contacting proximal connectors and means for changing the pattern of conductive contact between said proximal connectors and said terminals to conductively connect said terminals to selected distal electrodes.

21. A body tissue stimulation apparatus, comprising:

a body implantable tissue stimulator for generating electrical stimulation signals;

a body implantable lead assembly for sealingly and conductively engaging said tissue stimulator and for applying said stimulation signals to a predetermined site of the body;

said lead assembly including, at least two distal electrodes positioned at said site for applying said stimulation signals;

at least two spaced coaxially aligned proximal connectors; and means for conductively connecting one of said distal electrodes to two of said proximal connectors and the other of said distal electrodes to the third proximal connector;

said tissue stimulator including at least two terminals for conductively contacting proximal connectors and means for changing the position of the proximal connectors with respect to said terminals to conductively connect said terminals to selected distal electrodes.

22. The apparatus of claim 21, wherein said third proximal connector is positioned between said two proximal connectors.

23. A body implantable tissue stimulation system comprising:

a body implantable lead comprising:

first and second distal electrodes;

a proximal electrode assembly which comprises first and second coaxial, axially spaced proximal electrodes, each of which is electrically connected with a respective one of the distal electrodes;

first insulating means for electrically insulating the first proximal electrode from the second proximal electrode;

a third coaxial axially spaced proximal electrode electrically connected with the first proximal electrode and situated such that the second proximal electrode is interposed between the first and third proximal electrodes;

second insulating means for electrically insulating the third proximal electrode from the second proximal electrode; and a body implantable tissue stimulator comprising:

first and second stimulator electrodes; and means for defining a channel in the stimulator adjacent the stimulator electrodes to receive the proximal electrode assembly in order to establish electrical contact between the stimulator electrodes and respective ones of the proximal electrodes; and means for sealing the proximal electrode assembly in said channel, said means for sealing including

*means disposed between the first and second proximal electrodes for maintaining fluid isolation between the first and second proximal electrodes.*

*24. The system of claim 23, wherein said means for sealing includes at least one fluid sealing rib formed on at least one of the insulating means and extending radially outwardly from the proximal electrodes for contacting and sealing against the channel defining means.*

*25. The system of claim 23, wherein said sealing means comprises at least one fluid sealing rib mounted on said insulating means and extending outwardly from the proximal electrodes for contacting and sealing against the channel defining means, and wherein the system further comprises at least one fluid sealing rib mounted on the second insulating means and extending outwardly from the proximal electrodes for contacting and sealing against the channel defining means.*

* * * * *